US010231859B1

(12) United States Patent
Thorne et al.

(10) Patent No.: US 10,231,859 B1
(45) Date of Patent: Mar. 19, 2019

(54) BRACE SYSTEM (71) Applicant: Boston Dynamics, Inc., Waltham, MA (US)

(72) Inventors: Christopher Everett Thorne, Mountain View, CA (US); Steven D. Potter, Mountain View, CA (US); Michael Patrick Murphy, Mountain View, CA (US)

(73) Assignee: Boston Dynamics, Inc., Waltham, MA (US)

( * ) Notice: Subject to any disclaimer, the term of this patent is extended or adjusted under 35 U.S.C. 154(b) by 1023 days.

(21) Appl. No.: 14/266,989

(22) Filed: May 1, 2014

(51) Int. Cl.
*A61H 3/00* (2006.01)
*A61F 5/01* (2006.01)

(52) U.S. Cl.
CPC .............. *A61F 5/0102* (2013.01); *A61H 3/00* (2013.01)

(58) Field of Classification Search
CPC .... A61F 5/0102; A61F 5/0123; A61F 5/0125; A61F 2005/0132; A61F 2005/0137; A61F 2005/0144; A61F 2005/0146; B66D 2700/026; B25J 9/0006; B25J 9/104; B25J 9/1045; A61H 3/00; A61H 1/0262; A61H 1/024; Y10T 74/18848; A61B 34/71; A61B 2034/715
USPC ............... 74/490.01, 490.02, 490.04, 490.05
See application file for complete search history.

(56) References Cited

U.S. PATENT DOCUMENTS

| | | | | |
|---|---|---|---|---|
| 3,976,206 A | * | 8/1976 | Flatau | B25J 3/00 294/86.4 |
| 4,370,977 A | | 2/1983 | Driver | |
| 4,573,455 A | * | 3/1986 | Hoy | A61F 5/0123 602/16 |
| 4,604,098 A | * | 8/1986 | Seamone | A61F 2/582 623/60 |
| 4,697,808 A | * | 10/1987 | Larson | A61F 5/0102 482/4 |
| 4,844,057 A | * | 7/1989 | Hoy | A61F 5/0123 2/24 |
| 5,213,094 A | * | 5/1993 | Bonutti | A61F 5/0123 601/33 |
| 5,472,410 A | * | 12/1995 | Hamersly | A61F 5/0125 601/33 |

(Continued)

OTHER PUBLICATIONS

Jeon Do Young et al., Tendon-Driven Exoskeletal Power Assistive Robot and Driving Method Thereof (KR 1020110003596). Jul. 23, 2012. Human Translation.*

*Primary Examiner* — Michael J Tsai
*Assistant Examiner* — Christopher E Miller
(74) *Attorney, Agent, or Firm* — Honigman LLP (57) ABSTRACT

The present disclosure provides a brace system including an upper portion and a lower portion. The brace system may also include a first pulley rotatably coupling the upper portion to a first intermediate link positioned between the upper portion and the lower portion. The brace system may also include a second pulley rotatably coupling the first intermediate link to a second intermediate link positioned between the upper portion and the lower portion. The brace system may also include a third pulley rotatably coupling the second intermediate link to the lower portion. Further, the brace system may include at least one tension-bearing element substantially encircling each of the first pulley, the second pulley, and the third pulley.

19 Claims, 7 Drawing Sheets

(56) References Cited

U.S. PATENT DOCUMENTS

| | | | | |
|---|---|---|---|---|
| 5,476,358 A | * | 12/1995 | Costa | B25J 9/023 414/749.1 |
| 5,570,920 A | * | 11/1996 | Crisman | B25J 15/0009 294/111 |
| 5,662,693 A | * | 9/1997 | Johnson | A61F 5/01 607/48 |
| 5,828,813 A | * | 10/1998 | Ohm | B25J 3/04 700/260 |
| 5,891,061 A | | 4/1999 | Kaiser | |
| RE37,209 E | | 6/2001 | Hensley | |
| 6,969,363 B2 | | 11/2005 | Thuasne | |
| 7,153,242 B2 | * | 12/2006 | Goffer | A61F 5/0102 482/66 |
| 7,648,436 B2 | * | 1/2010 | Horst | F16H 19/005 474/117 |
| 8,662,552 B2 | * | 3/2014 | Torres-Jara | B25J 13/084 294/111 |
| 8,910,984 B2 | * | 12/2014 | Akae | B25J 15/0009 294/106 |
| 2002/0133108 A1 | | 9/2002 | Jagodzinski | |
| 2003/0212356 A1 | * | 11/2003 | Scorvo | A61F 5/0125 602/20 |
| 2004/0199147 A1 | * | 10/2004 | Nishizawa | A61B 17/062 606/1 |
| 2006/0094989 A1 | * | 5/2006 | Scott | A61F 2/54 601/5 |
| 2006/0276728 A1 | * | 12/2006 | Ashihara | A61F 5/0102 601/5 |
| 2007/0089557 A1 | * | 4/2007 | Solomon | B25J 9/1045 74/490.01 |
| 2007/0199399 A1 | * | 8/2007 | Okazaki | B25J 9/104 74/490.05 |
| 2008/0009771 A1 | * | 1/2008 | Perry | B25J 9/0006 600/587 |
| 2008/0255489 A1 | | 10/2008 | Genda et al. | |
| 2008/0288107 A1 | * | 11/2008 | Tokita | A61H 1/0237 700/245 |
| 2008/0289670 A1 | * | 11/2008 | Ashihara | B25J 9/0006 135/65 |
| 2010/0050765 A1 | * | 3/2010 | Kadota | A61B 5/1071 73/379.01 |
| 2010/0170362 A1 | * | 7/2010 | Bennett | A61B 17/32002 74/490.04 |
| 2010/0249818 A1 | * | 9/2010 | Jinno | A61B 17/29 606/174 |
| 2010/0280662 A1 | * | 11/2010 | Abdallah | H01R 13/17 700/261 |
| 2011/0098618 A1 | * | 4/2011 | Fleming | A61F 5/0123 602/16 |
| 2012/0330198 A1 | * | 12/2012 | Patoglu | B25J 9/0006 601/33 |
| 2013/0190669 A1 | | 7/2013 | Rokosz | |
| 2013/0245522 A1 | | 9/2013 | Modglin | |
| 2013/0245524 A1 | * | 9/2013 | Schofield | A61F 5/0125 602/16 |
| 2013/0304084 A1 | * | 11/2013 | Beira | A61B 19/2203 606/130 |
| 2014/0100492 A1 | * | 4/2014 | Nagasaka | A61B 5/061 601/34 |
| 2015/0051527 A1 | * | 2/2015 | Potter | A61F 5/0125 602/16 |
| 2015/0167798 A1 | * | 6/2015 | Gosselin | B25J 9/102 74/490.04 |
| 2015/0190249 A1 | * | 7/2015 | Ishibashi | A61H 3/00 623/24 |
| 2015/0223959 A1 | * | 8/2015 | Cempini | A61H 1/0285 602/22 |
| 2015/0272811 A1 | * | 10/2015 | Choi | B25J 17/00 623/27 |
| 2015/0374573 A1 | * | 12/2015 | Horst | A61H 3/00 602/16 |

* cited by examiner

BRACE SYSTEM

GOVERNMENT RIGHTS

This invention was made with U.S. Government support under Contract No. W911QX-12-C-0085 awarded by DARPA. The Government may have certain rights with regard to the invention.

BACKGROUND

Unless otherwise indicated herein, the materials described in this section are not prior art to the claims in this application and are not admitted to be prior art by inclusion in this section.

Many existing braces, such as knee braces, are designed with rehabilitation in mind. Typically, natural knee joint motion is inhibited or constrained in some way. There is a different need, however, for new knee and other joint braces which can be used for other purposes. In one example, a person wearing a heavy backpack might benefit from a knee brace which not only provides stability but also reduces the load on the muscles of the knee, particularly the quadriceps. Indeed, when the knee bends, it would be beneficial to lower the load carried by the knee by applying an external extension torque. Energy stored during the bending action can be used to straighten the knee as well. When the leg swings forward for the next step, it would be advantageous if the knee brace applied appropriate flexion torque to help lift the foot, or that the brace operated freely, applying minimal torque to the leg.

Existing braces using one degree of freedom (DOF) hinges may be sensitive to alignment of the brace to the knee joint. This can be a problem for assistive (torque-producing) braces. Mismatch between the instantaneous center of rotation of the hinge and of the knee causes uncomfortable or dangerous loads on the knee as well as making the brace migrate down the leg. The mismatch may occur because the one DOF hinges are only an approximation of the motion of the knee and because of deflection of the flesh where the brace attaches to the leg.

Other existing braces may require rigid structure spanning between the medial and lateral hinges. This enforces a fixed width and makes the brace wider than might be necessary since it accommodates the width of the knee at the desired maximum flexion position. To avoid a sloppy fit and interference of the braces of the left and right legs, these braces typically require custom fitting to each user. Still other example braces may not allow twisting of the foreleg and can restrict a normal DOF of the leg. Such braces can be awkward to use and increase the likelihood of chafing and migration of the brace. Therefore, an improved brace system may be desirable.

SUMMARY

Example brace systems described herein apply flexion and/or extension torque to a joint while allowing the normal motion of the joint. A brace system may include a medial brace and a lateral brace. The medial and lateral braces may be substantially similar, although some differences may be present to better form to the desired joint. In another example, the brace system may include one of a medial or lateral brace. An example brace may include an upper portion, a lower portion, and a hinge assembly. The upper portion and lower portion are configured to attach to the upper and lower limbs of a human or animal joint and are pivotably connected to the hinge assembly. In one example, the hinge assembly may include two or more intermediate links.

The brace system may also include two or more pulleys positioned between the upper portion and the lower portion. The brace system may further include a tension-bearing element substantially encircling each of the pulleys that may be anchored to the lower portion. In one embodiment, the tension-bearing element may be wrapped around the pulleys in a clockwise direction. In this configuration, the tension-bearing element may apply an extension torque to the brace system. In an alternative configuration, the tension-bearing element may be wrapped around the pulleys in a counter-clockwise direction. In this configuration, the tension-bearing element may apply a flexion torque to the brace system. In yet another configuration, two tension-bearing elements may be wrapped around the pulleys in opposite directions. A first tension-bearing element may be wrapped around the pulleys in a clockwise direction to apply an extension torque, and a second tension-bearing element may be wrapped around the pulleys in a counterclockwise direction to apply a flexion torque. Other embodiments are possible as well.

In one embodiment, the present disclosure provides a brace system including an upper portion and a lower portion. The brace system may also include a first pulley rotatably coupling the upper portion to a first intermediate link positioned between the upper portion and the lower portion. The brace system may also include a second pulley rotatably coupling the first intermediate link to a second intermediate link positioned between the upper portion and the lower portion. The brace system may also include a third pulley rotatably coupling the second intermediate link to the lower portion. Further, the brace system may include at least one tension-bearing element substantially encircling each of the first pulley, the second pulley, and the third pulley.

In another embodiment, the present disclosure provides a brace system including an upper portion and a lower portion. The brace system may also include a first pulley rotatably coupling the upper portion to an intermediate link positioned between the upper portion and the lower portion. The brace system may also include a second pulley rotatably coupling the intermediate link to the lower portion. Further, the brace system may include at least one tension-bearing element substantially encircling each of the first pulley and the second pulley.

In yet another embodiment, the present disclosure provides a brace system including an upper portion and a lower portion. The brace system may also include a first pulley rotatably coupling the upper portion to a first intermediate link positioned between the upper portion and the lower portion. The brace system may also include a second pulley rotatably coupling the first intermediate link to a second intermediate link positioned between the upper portion and the lower portion. The brace system may also include a third pulley rotatably coupling the second intermediate link to the lower portion. The brace system may include at least one tension-bearing element substantially encircling each of the first pulley, the second pulley, and the third pulley. Further, the brace system may also include an actuator system coupled to the at least one tension-bearing element, wherein the actuator system is configured to apply a torque to the brace system.

These as well as other aspects, advantages, and alternatives will become apparent to those of ordinary skill in the art by reading the following detailed description, with reference where appropriate to the accompanying drawings.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Many existing braces are designed with rehabilitation in mind, such that natural knee joint motion is inhibited or constrained in some way. There is a different need, however, for assistive (torque-producing) braces. For example, a person wearing a heavy backpack might benefit from a knee brace which not only provides stability but also reduces the load on the knees of the wearer. Example brace systems described herein apply flexion and/or extension torque to a joint while allowing the normal motion of the joint. In accordance with the described embodiments, a flexion or extension torque is applied to a joint (e.g., knee, ankle, finger joint, or the like) while allowing the normal motion of the joint. For instance, to assist the knee joint, a torque is applied to the thigh and an equal and opposite torque is applied to the foreleg.

It should be understood that the above examples are provided for illustrative purposes, and should not be construed as limiting. As such, the method may additionally or alternatively includes other features or includes fewer features, without departing from the scope of the invention.

Figure 1:
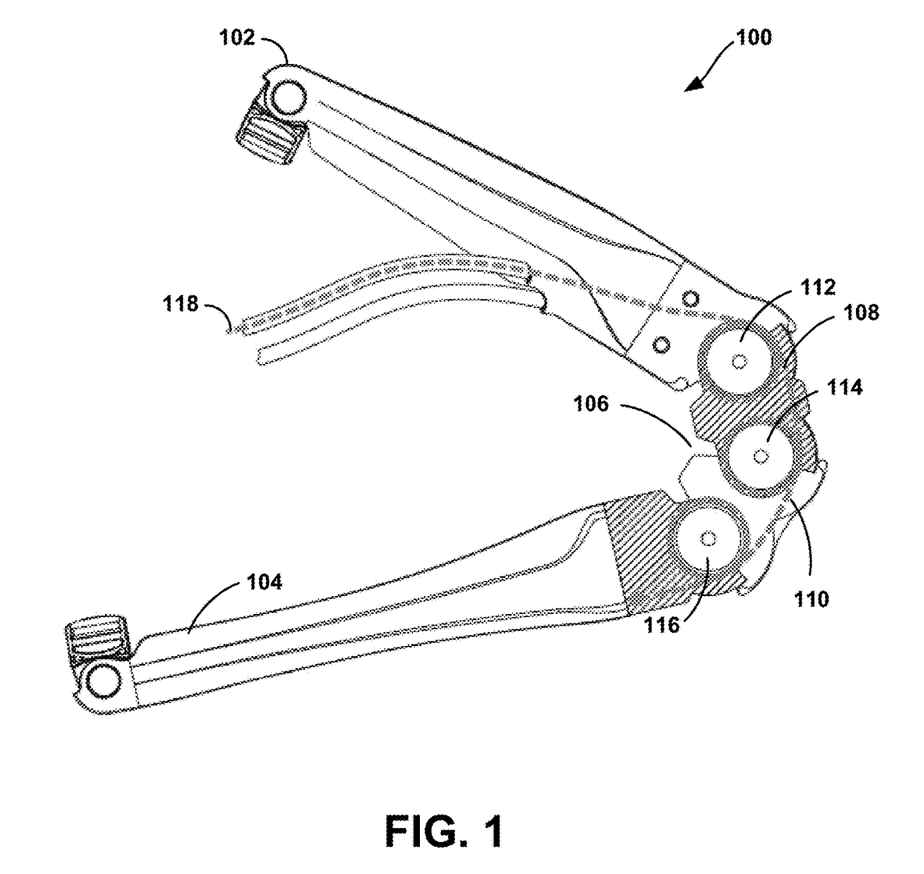
FIG. 1 is a side view of a brace system according to an example embodiment.

Systems and devices in which example embodiments may be implemented will now be described in greater detail. FIG. 1 illustrates a side view of one example brace 100 of an example brace system. The brace system may comprise a single brace positioned on the desired joint, or may include a medial brace and a lateral brace. The medial and lateral braces are securable about a leg, for example, via cross members. The cross-members may include fabric with Velcro or other fasteners, plastic sleeve type configurations, or the like. In one example, the cross-members are made of pliable material (e.g., fabric) so the medial and lateral braces can taper inwardly to better follow the contours of the knee or other joint. The medial and lateral braces may be substantially similar, although some differences may be present to better form to the desired joint.

As shown in FIG. 1, each brace may include an upper portion 102, a lower portion 104, and a hinge assembly 106. The upper portion 102 and lower portion 104 are configured to attach to the upper and lower limbs of a human or animal joint and are rotatably connected to the hinge assembly 106. The upper portion 102 and lower portion 104 may include carbon fiber material, plastic, metal, or a combination of materials. The hinge assembly 106 as shown in FIG. 1 may include two or more intermediate links 108, 110. The use of two or more intermediate links allows planar/parallel motion of the lower portion 104 relative to the upper portion 102. This makes the brace 100 less sensitive to fore-aft misalignment. In effect, the hinge assembly 106 can stretch and contract in the longitudinal direction.

The brace 100 may also include a first pulley 112 rotatably coupling the upper portion 102 to the first intermediate link 108, a second pulley 114 rotatably coupling the first intermediate link 108 to the second intermediate link 110, and a third pulley rotatably coupling the second intermediate link 110 to the lower portion 104. Each of the three pulleys 112, 114, and 116 may be positioned between the upper portion 102 and the lower portion 104.

The brace 100 may further include a tension-bearing element 118 that substantially encompasses the pulleys 112, 114, and 116 and may be anchored to the lower portion 104. Each of the pulleys 112, 114, and 116 may be coupled to the brace 100 via a pin, or other rotatable member such that each of the upper portion 102, the first intermediate link 108, the second intermediate link 110, and the lower portion 104 may rotate independent to one another. The pulleys 112, 114, and 116, and intermediate links 108 and 110 form a parallel-action mechanism which provides substantially parallel motion of the lower portion 102 with respect to the upper portion 104 without extending or retracting the tension-bearing element 118. These two translational DOF are non-actuated, meaning that they can happen freely (except for friction) even when the tension-bearing element 118 is under load and the brace 100 is exerting torques on the limbs adjacent to the joint. The two translational DOF make the brace 100 far less sensitive to alignment with the body and avoid shear loading of the knee. "Pistoning" forces (along the long axes of the upper portion 102 and lower portion 104) are also largely avoided, which minimizes the tendency of the brace to migrate, e.g. shift down the leg while walking. Further, the two translational DOF allow the brace 100 to fit individuals of many sizes, thereby reducing the need for a customized brace for each use case. In addition, the tension-bearing element 118 substantially encompassing the pulleys 112, 114, and 116 enables the angle between the upper portion 102 and the lower portion 104 to extend beyond 180 degrees. Such a capability may be advantageous to measure hyperextension of a joint, as an example. As another example, it may be advantageous for the hinge assembly 106 to be aligned on a user in a way that the hinge assembly 106 is hyperextended in a user's resting extension position. In such a case, it would be advantageous to be able to apply torque to the brace 100 beyond 180 degrees.

In general, it should be understood that the parallel-action mechanisms described herein do not have to be perfect. Some deviation from parallel motion may even be desirable, e.g. to make the links of the hinge assembly 106 open in a certain order, or to compensate for friction. As long as the hinge action produces approximately parallel motion of the lower portion 104 with respect to the upper portion 102, the translational forces applied to the arms of the brace 100 by the hinge assembly 106 will be small, even when the brace is under load.

The pulleys 112, 114, and 116 may have various configurations. In one example, the pulleys 112, 114, and 116 may be rotating pulleys that rotate as the tension-bearing element 118 moves over the pulley. In another example, the pulleys 112, 114, and 116 may be fixed pulleys with a low-friction surface configured to enable the tension-bearing element 118 to slide over the pulley. The tension-bearing element 118 may include a cable, a cord, a belt or a band, as examples. The tension-bearing element 118 may be used to apply a torque to the brace or simply to measure the knee angle without ever applying torques, as discussed in more detail below. In another example, each of the pulleys 112, 114, and 116 may include sprocket teeth 117, and the tension-bearing element 118 may include a chain 119. Other examples are possible as well.

In another configuration, the brace 100 may only include a single intermediate link positioned between the upper portion 102 and the lower portion 104. In such an embodiment, the brace 100 may also include a first pulley rotatably coupling the upper portion 102 to the single intermediate link, and a second pulley rotatably coupling the single intermediate link to the lower portion 104. The single intermediate link may be configured with at least one non-actuated degree of freedom in addition to flexion and extension allowing translation of the upper portion 102 with respect to the lower portion 104. In the knee brace example, this DOF mitigates vertical misalignment of the brace and minimizes shear loads on the knee, but is less effective for fore/aft misalignment and the resulting pistoning forces. The brace 100 may also include at least one tension-bearing element 118 substantially encircling each of the first pulley and the second pulley.

In yet another embodiment, the brace 100 may include four or more pulleys. As a specific example, if four pulleys are used, the brace 100 may include three intermediate links positioned between the four pulleys. In such an embodiment, the brace 100 may also include a first pulley rotatably coupling the upper portion 102 to a first intermediate link, a second pulley rotatably coupling the first intermediate link to a second intermediate link, a third pulley rotatably coupling the second intermediate link to a third intermediate link, and a fourth pulley rotatably coupling the third intermediate link to the lower portion 104. The brace 100 may also include at least one tension-bearing element 118 substantially encircling each of the first pulley, the second pulley, the third pulley and the fourth pulley. Other numbers of pulleys are possible as well. For a brace having n pulleys, the brace may include n−1 intermediate links positioned between the n pulleys, and a tension-bearing element substantially encircling each of the n pulleys.

In the example shown in FIG. 1, the tension-bearing element 118 is wrapped around the pulleys 112, 114, and 116 in a clockwise direction. The tension-bearing element 118 completes a full rotation around each of the pulleys 112, 114, and 116. However, it is possible for the tension-bearing element 118 to be slightly less than a full rotation around each of the pulleys 112, 114, and 116. In another example, the tension-bearing element 118 may be wrapped around the pulleys 112, 114, and 116 a number of times. In the configuration shown in FIG. 1, as tension is applied to the tension-bearing element 118, the angle between the upper portion 102 and the lower portion 104 increases, thereby applying an extension torque to the brace 100. In addition to applying an extension torque, the tension-bearing element 118 may be coupled to a measurement system configured to measure the angle of the joint. The measurement system may be in communication with a processor on a computing device, which may in turn process the joint angle data and apply an extension torque in response to the joint angle data. For example, the measurement system may convey joint data information to the processor that the knee joint is fully flexed, and the processor may then instruct the brace 100 to apply an extension torque to straighten the knee joint.

The measurement system may use the tension-bearing element 118 to measure the angle of the joint by a change in length across the hinge assembly 106. In particular, the measurement system may measure the motion of the tension-bearing element 118 on the non-anchored side of the brace 100. The measurement system may determine a joint angle based on the measured motion of the tension-bearing element 118. In another example, the measurement system may be configured to measure the change in length of the tension-bearing element 118 or another non-tension bearing element across one or more of the pulleys 112, 114, 118. In yet another example, the measurement system may be configured to measure the change in rotation of one or more of the pulleys 112, 114, 118. Other examples are possible as well.

Figure 2:
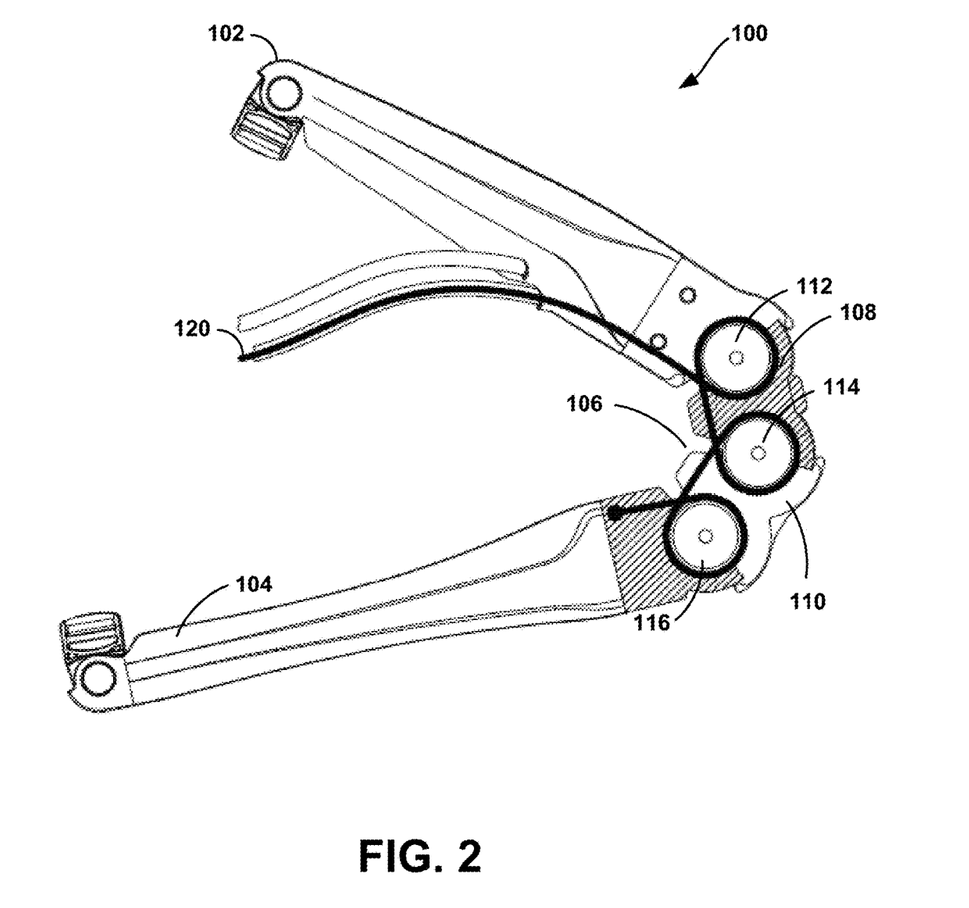
FIG. 2 is a side view of a brace system according to another example embodiment.

FIG. 2 illustrates an alternative configuration, in which the tension-bearing element 120 is wrapped around the pulleys 112, 114, and 116 in a counterclockwise direction. Similar to the tension-bearing element 118 illustrated in FIG. 1, the tension-bearing element 120 in FIG. 2 completes a full rotation around each of the pulleys 112, 114, and 116. However, it is possible for the tension-bearing element 120 to be slightly less than a full rotation around each of the pulleys 112, 114, and 116. In another example, the tension-bearing element 120 may be wrapped around the pulleys 112, 114, and 116 a number of times. In the configuration shown in FIG. 2, as tension is applied to the tension-bearing element 120, the angle between the upper portion 102 and the lower portion 104 decreases, thereby applying a flexion torque to the brace 100. In addition to applying a flexion torque, the tension-bearing element 120 may be coupled to a measurement system configured to measure the angle of the joint. The measurement system may be in communication with a processor on a computing device, which may in turn process the joint angle data and apply flexion torque in response to the joint angle data. For example, the measurement system may convey joint data information to the processor that the knee joint is fully extended, and the processor may then instruct the brace 100 to apply flexion torque to bend the knee joint.

Figure 3:
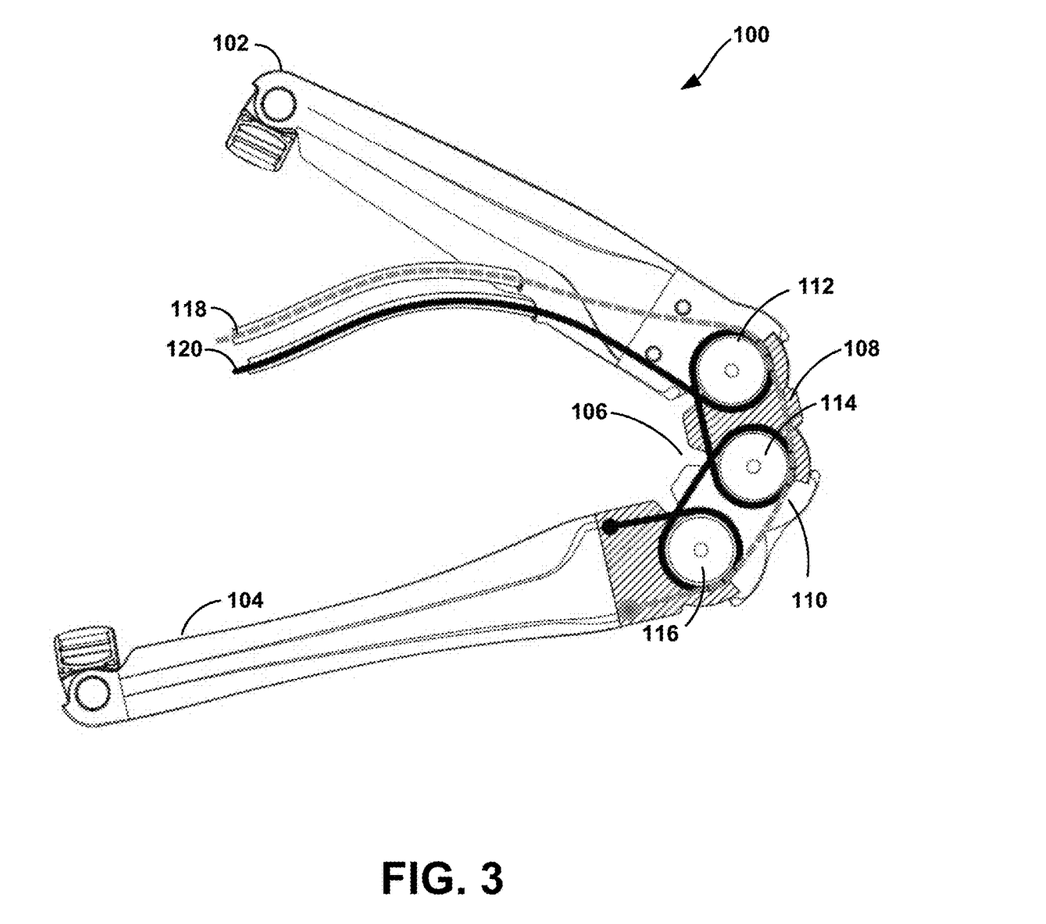
FIG. 3 is a side view of a brace system according to yet another example embodiment.

FIG. 3 illustrates an alternative configuration, in which two tension-bearing elements 118, 120 are substantially encircling the pulleys 112, 114, and 116. A first tension-bearing element 118 is wrapped around the outside of pulleys 112, 114, and 116, and a second tension-bearing element 120 is wrapped around the pulleys 112, 114, and 116 in a counterclockwise direction to apply a flexion torque to the brace system 100. The first tension-bearing element 118 may be coupled to a measurement system to measure the angle of the joint, as discussed above. In another embodiment, the first tension-bearing element may be wrapped around the pulleys 112, 114, and 116 in a clockwise direction to apply an extension torque to the brace system 100, and the second tension-bearing element 120 may be wrapped around the outside of pulleys 112, 114, and 116 and may be coupled to a measurement system to measure the angle of the joint.

Figure 4:
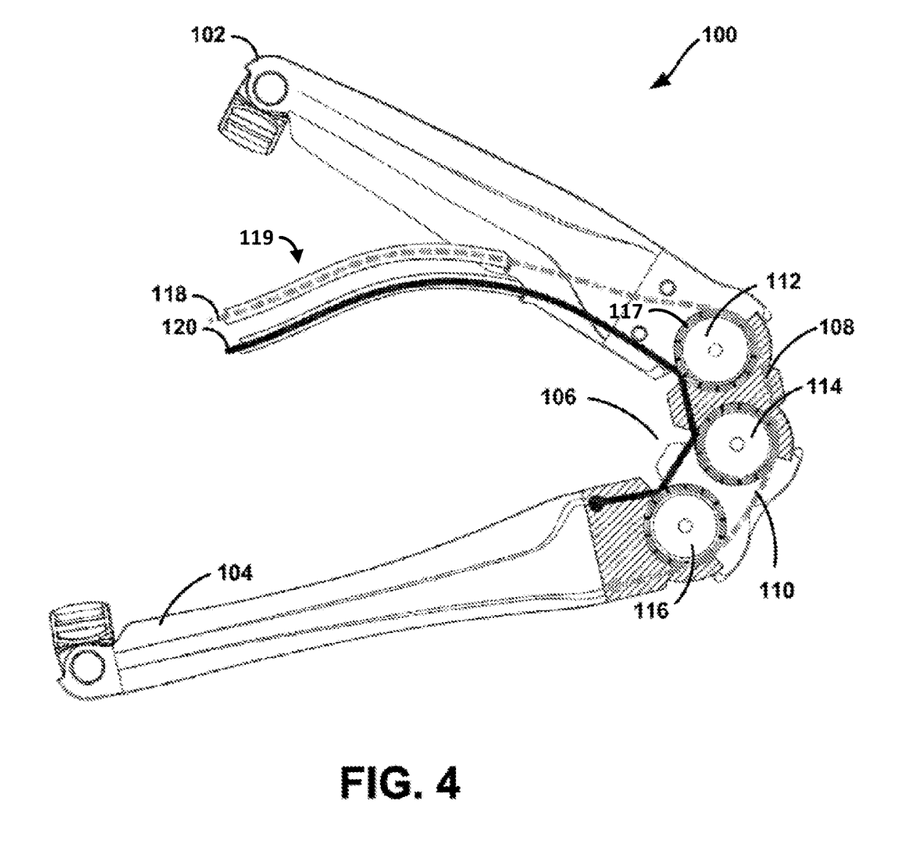
FIG. 4 is a side view of a brace system according to yet another example embodiment.

FIG. 4 illustrates another alternative configuration, in which the two tension-bearing elements 118, 120 are wrapped around the pulleys 112, 114, and 116. A first tension-bearing element 118 is wrapped around the pulleys 112, 114, and 116 in a clockwise direction to apply an extension torque to the brace system 100, and a second tension-bearing element 120 is wrapped around the pulleys 112, 114, and 116 in a counterclockwise direction to apply a flexion torque to the brace system 100. The pulleys 112, 114, and 116 may include a separate track for each tension-bearing element so that the first tension-bearing element 118 and the second tension-bearing element 120 do not tangle. In another example, each of the pulleys 112, 114, and 116 may include multiple separate pulleys each sharing a common axis of rotation. Other embodiments are possible as well.

The first tension-bearing element 118 and the second tension-bearing element 120 may be coupled to a measurement system configured to measure the angle of the joint. The measurement system may be in communication with a processor on a computing device, which may in turn process the joint angle data and apply a torque in response to the joint angle data. In one example, the brace 100 may use the second tension-bearing element 120 to measure the joint angle when the brace 100 is applying an extension torque using the first tension-bearing element 118. Similarly, the brace 100 may use the first tension-bearing element 118 to measure the joint angle when the brace 100 is applying a flexion torque using the second tension-bearing element 120.

In another embodiment, additional tension-bearing elements may be placed over the pulleys 112, 114, and 116 and coupled to a measurement system to measure the angle of the joint. For example, one set of tension-bearing elements may be wrapped around the pulleys 112, 114, and 116 to apply extension and/or flexion torques to the brace 100, and a second set of tension-bearing elements may be wrapped around the pulleys 112, 114, and 116 to measure the joint angle. Other embodiments are possible as well.

Figure 5:
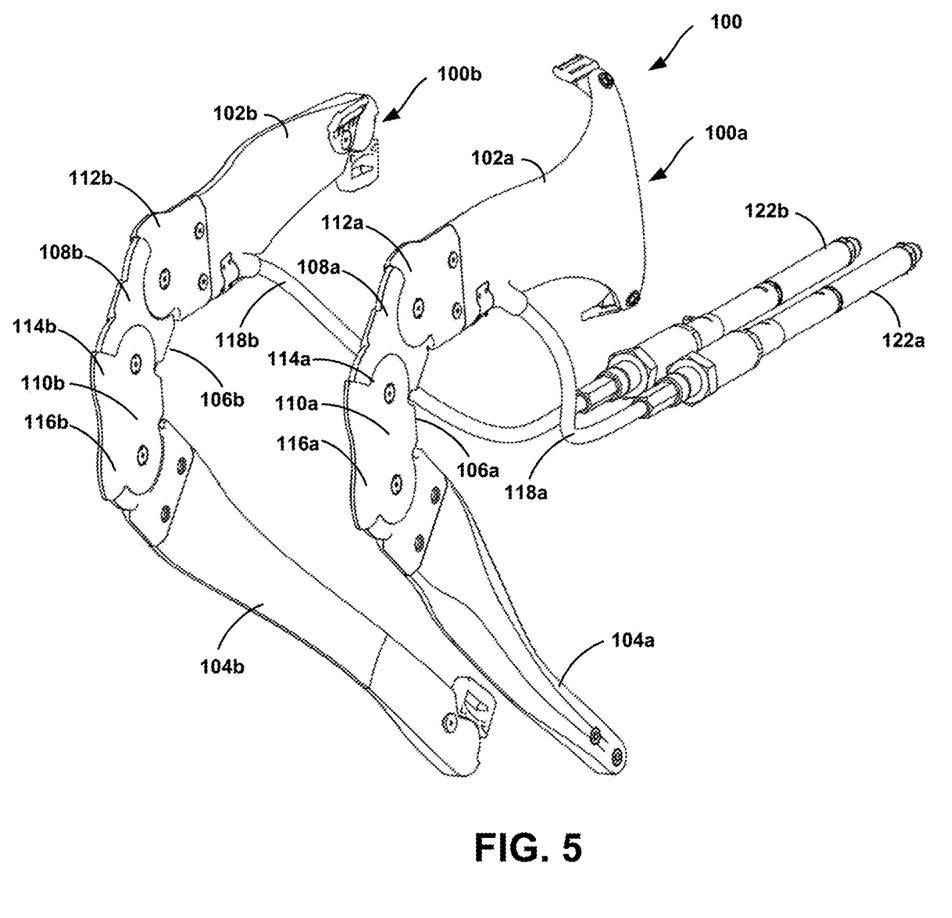
FIG. 5 illustrates a brace system including an actuator system according to an example embodiment.

FIG. 5 illustrates a brace system 100 including a medial brace 100a and a lateral brace 100b. As shown in FIG. 5, the each of the medial brace 100a and the lateral brace 100b may include all of the features described in FIG. 1. Further, the medial brace 100a is shown having a slightly larger upper section 102a so as to better conform to the inside of a wearer's thigh. The brace system 100 of FIG. 5 also includes two actuators 122a, 122b according to an example embodiment. In this example, there is one tension-bearing element 118a, 118b coupled to each of the actuators 122a, 122b. The tension bearing elements 118a, 118b may be substantially encircling the pulleys 112, 114, and 116 to apply either an extension torque (using the configuration shown in FIG. 1) or a flexion torque (using the configuration shown in FIG. 2) to the brace system 100. The actuators 122a, 122b may be hydraulic actuators, or pneumatic actuators, as examples. Further, the actuators 122a, 122b may be in fluid communication so that the pressure between the two actuators 122a, 122b equalizes, thereby ensuring that the same torque is applied to each of the medial brace 100a and lateral brace 100b of the brace system 100. Other example actuator configurations are possible as well.

Figure 6:
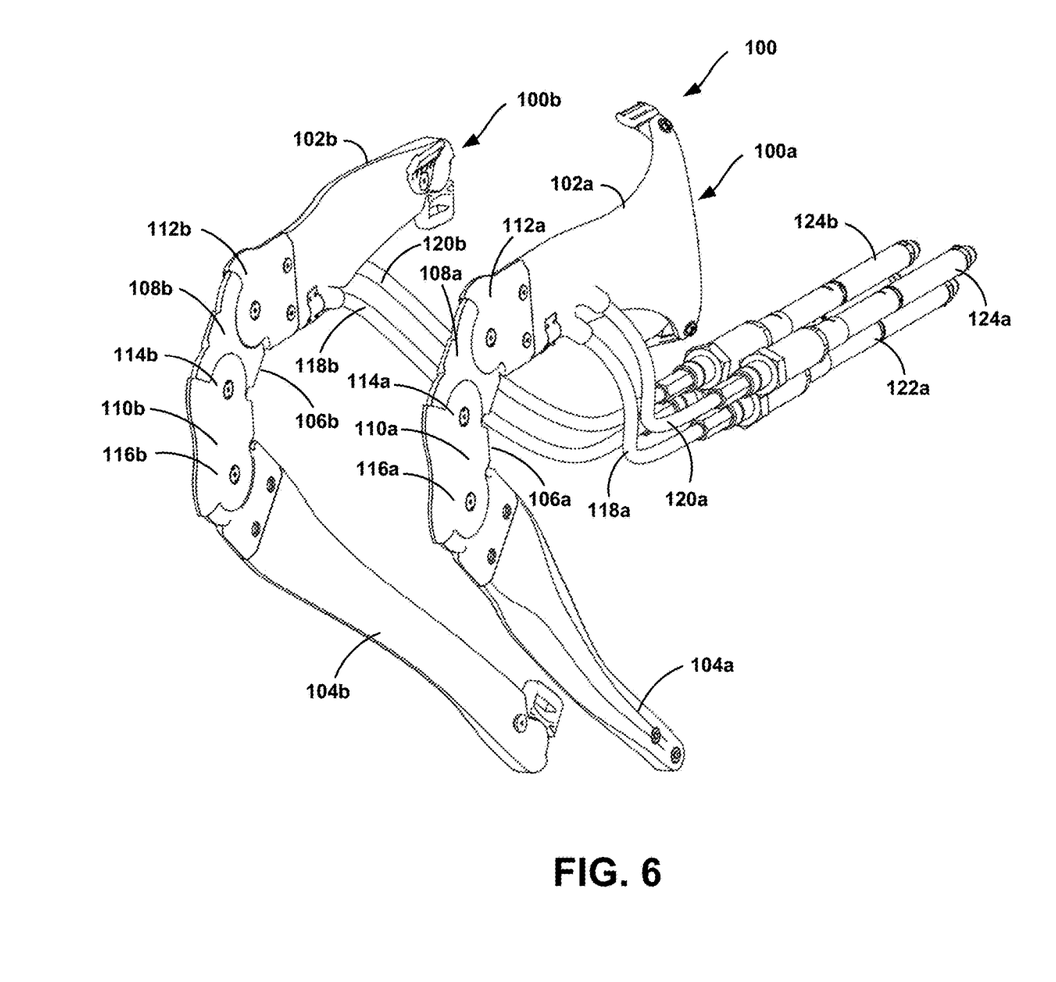
FIG. 6 illustrates a brace system including an actuator system according to another example embodiment.

FIG. 6 illustrates a brace system 100 including an actuator system according to another example embodiment. In FIG. 6, the brace system includes four actuators 122a, 124a, 122b, and 124b. Actuator 122a may be coupled to tension-bearing member 118a to apply an extension torque to the medial brace 100a of the brace system 100. Actuator 124a may be coupled to tension-bearing member 120a to apply flexion torque to the medial brace 100a of the brace system 100. Similarly, actuator 122b may be coupled to tension-bearing member 118b to apply an extension torque to the lateral brace 100b of the brace system 100, and actuator 124b may be coupled to tension-bearing member 120b to apply flexion torque to the lateral brace 100b of the brace system 100. The actuators 122, 124 may be hydraulic actuators or pneumatic actuators, among other possibilities as discussed above.

The actuators described above in relation to FIGS. 5 and 6 may be coupled to a hydraulic circuit to assist in various actions. In one example, the hydraulic circuit may be intended to assist walking with a heavy pack. In this example, the brace system 100 may include position sensors and pressure sensors to provide knee position and torque data to a controller (e.g., a microprocessor, FPGA, microcontroller, or the like). Based on these inputs and knowledge of typical walking gait cycles, the controller may be programmed to close a valve in the actuator just prior to heel-strike. At heel-strike, the leg bends and forces fluid in the actuators. In effect, the brace acts like a spring during this phase of the gait cycle, called the "weight acceptance phase". The knee and brace flex, storing energy in the actuator. Later in stance when the knee extends, pressurized fluid in the actuator assists the knee extensor muscles. If the knee extends further than its angle at heel-strike, pressure will drop below that of the actuator and fluid will flow allowing the knee to extend freely. Late in stance, knee extension velocity goes to zero (as the knee changes direction) and the controller may be programmed to open a valve to allow free flow of fluid in the actuator. This allows the leg to freely flex to provide ground clearance during the swing phase of the gait cycle.

Other hydraulic circuits are possible and can be tailored for other behaviors, such as walking downhill, stair descent, etc. Circuits may also be designed to store energy on descent and use this energy for assisting ascent. Auxiliary power sources such as electric motors or fuel-driven engines can be used to enable sustained climbing, jumping etc. Other sensors such as foot force sensors, accelerometers, electromyography sensors, nerve implants, brain implants, etc. may be used as inputs to a controller which can modulate the force in actuators thus modulating the torque applied by the brace to the wearer.

Figure 7:
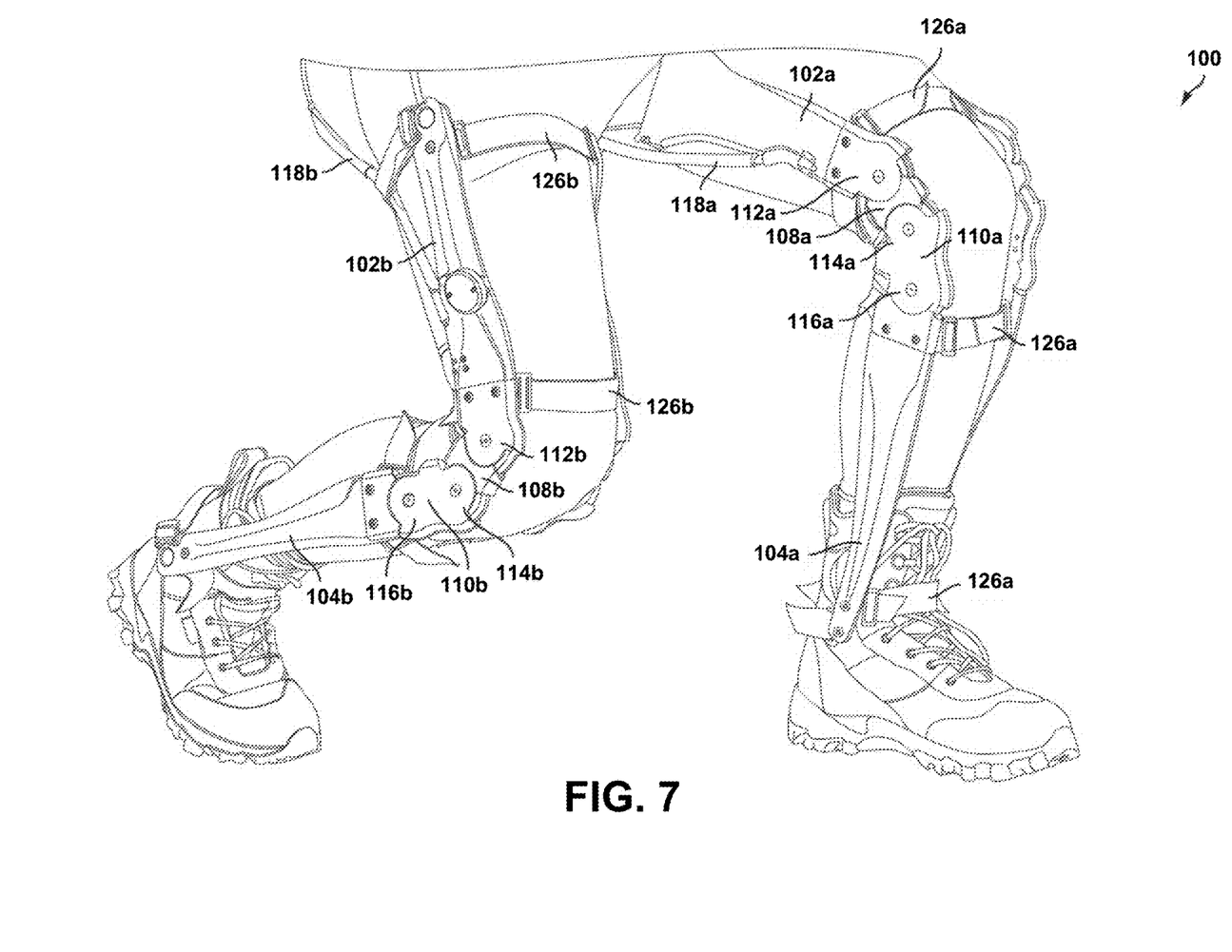
FIG. 7 is an example brace system being worn by a user.

FIG. 7 illustrates a wearer with two brace systems, each having a medial brace and a lateral brace. The illustration of FIG. 7 shows a viewpoint in which the medial brace is shown on the left leg of the wearer, and the lateral brace is shown on the right leg of the wearer. However, in this embodiment each leg has both a medial and lateral brace. Pliable cross members 126a, 126b are shown securing the lateral brace to the medial brace in each brace system. The pliable cross members 126a, 126b may include a Velcro and loop system to secure and tighten the brace on the wearer. In another example, the pliable cross members 126a, 126b may include buckles, snaps, or any other means for securing the medial and lateral braces. The cross members 126a, 126b may be pliable (e.g., fabric) so the medial and lateral braces can taper inwardly, to better follow the contours of the knee or other joint. In addition, cross members made of soft materials can be more easily integrated into clothing or worn under clothing.

Most existing braces do not allow twisting of the foreleg and thus restrict a normal DOF of the leg. This makes the braces awkward to use and increases the likelihood of chafing and migration of the brace. The use of pliable cross members enables the foreleg to twist in normal motion, thereby preventing chafing and discomfort for the wearer.

Further, the use of pliable cross-members reduces the size and weight of the brace and allows for width adjustment using straps. An additional advantage is that the hinge assemblies on the medial and lateral sides do not have to be parallel (as viewed from the front). The medial and lateral braces may angle inwardly as defined by the plane of the drawing page. Since people's legs and knees are generally tapered, this allows the hinge assemblies to lie closer to the knee which reduces the likelihood of interference with the brace on the opposite leg. Each hinge assembly lies in an angled plane as the joint approaches full extension.

FIGS. 1-7 illustrate an example brace system designed for a human knee. In such an example, the upper portion of the knee brace may be approximately the size of a human femur, and the lower portion may be approximately the size of a human tibia/fibula. However, there are many other possible implementations for the described brace system. In one example, the brace system described above in relation to FIG. 1-7 may be designed to fit a limb of a horse, or other animal. In such an example, the sizes of the various components may vary depending on the particular use case, while the interaction between components remains as described above. In another example, the brace system may be configured to fit on an elbow joint of a human. In such an example, the upper portion of the knee brace may be approximately the size of a human humerus, and the lower portion may be approximately the size of a human radius/ulna. Such a brace may be used to assist a wearer in lifting or unloading heavy objects, along with other potential use cases. Other examples are possible as well.

In yet another embodiment, the brace system described above in relation to FIGS. 1-7 may be designed for a robotic system. For example, the brace system may be used for the knee and elbow joints of a humanoid robot. As another example, the brace system may be used in a manufacturing robotic arm having an upper portion and a lower portion. Other examples are possible as well.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

We claim:

1. A brace system comprising:
   an upper portion;
   a lower portion;
   a first pulley rotatably coupling the upper portion to a first intermediate link to allow the upper portion and the first intermediate link to rotate independently of one another, wherein the first intermediate link is positioned between the upper portion and the lower portion;
   a second pulley rotatably coupling the first intermediate link to a second intermediate link, wherein the second intermediate link is positioned between the upper portion and the lower portion;
   a third pulley rotatably coupling the second intermediate link to the lower portion to allow the second intermediate link and the lower portion to rotate independently of one another; and
   a first tension-bearing element having a first end and a second end, the first tension-bearing element substantially encircling each of the first pulley, the second pulley, and the third pulley in a first direction, wherein the second end of the first tension-bearing element is anchored to the lower portion.

2. The brace system of claim 1, further comprising an actuator system coupled to the first end of the first tension-bearing element, wherein the actuator system is configured to apply a torque to the brace system.

3. The brace system of claim 2, wherein the actuator system includes a hydraulic actuator coupled to the first end of the first tension-bearing element.

4. The brace system of claim 1, wherein the brace system includes a medial brace and a lateral brace securable via pliable cross members.

5. The brace system of claim 1, wherein the first tension-bearing element comprises one of a cable, a cord, a belt or a band.

6. The brace system of claim 1, wherein each of the first pulley, the second pulley and the third pulley include sprocket teeth, and wherein the first tension-bearing element comprises a chain.

7. The brace system of claim 1, further comprising a second tension-bearing element having a first end and a second end, the second tension-bearing element substantially encircling each of the first pulley, the second pulley, and the third pulley in a second direction.

8. The brace system of claim 7, wherein the second end of the second tension-bearing element is anchored to the lower portion and the first end of the second tension-bearing element is coupled to an actuator, the actuator configured to apply a flexion torque to the brace system.

9. The brace system of claim 1, wherein the first end of the first tension-bearing element is coupled to an actuator, the actuator configured to apply an extension torque to the brace system.

10. The brace system of claim 1, further comprising a measurement system coupled to the first tension-bearing element, the measurement system configured to determine an angle of a joint on which the brace system is positioned by measuring at least one of:
    a motion of the first tension-bearing element on the upper portion;
    a change in length of the first tension-bearing element across one or more of the first pulley, the second pulley, or the third pulley; or
    a change in rotation of one or more of the first pulley, the second pulley, or the third pulley.

11. The brace system of claim 10, wherein the measurement system is in communication with a processor on a computing device, wherein the processor is configured to receive joint angle data from the measurement system, and wherein the processor is further configured to apply a torque to the brace system in response to the determined joint angle data.

12. A brace system comprising:
    an upper portion;
    a lower portion;
    a first pulley rotatably coupling the upper portion to an intermediate link to allow the upper portion and the intermediate link to rotate independently to one another, wherein the intermediate link is positioned between the upper portion and the lower portion;

a second pulley rotatably coupling the intermediate link to the lower portion to allow the lower portion and the intermediate link to rotate independently to one another; and a first tension-bearing element having a first end and a second end, the first tension-bearing element substantially encircling each of the first pulley and the second pulley in a first direction, wherein the second end of the first tension-bearing element is anchored to the lower portion.

13. The brace system of claim 12, wherein the intermediate link is configured with at least one non-actuated degree of freedom allowing translation of the lower portion with respect to the upper portion.

14. The brace system of claim 12, further comprising a second tension-bearing element having a first end and a second end, the second tension-bearing element substantially encircling each of the first pulley and the second pulley in a second direction.

15. The brace system of claim 14, wherein the second end of the second tension-bearing element is anchored to the lower portion and the first end of the second tension-bearing element is coupled to an actuator, the actuator configured to apply a flexion torque to the brace system.

16. The brace system of claim 12, wherein the first end of the first tension-bearing element is coupled to an actuator, the actuator configured to apply an extension torque to the brace system.

17. A brace system comprising:
an upper portion;
a lower portion;
a first pulley rotatably coupling the upper portion to a first intermediate link to allow the upper portion and the first intermediate link to rotate independently of one another, wherein the first intermediate link is positioned between the upper portion and the lower portion;
a second pulley rotatably coupling the first intermediate link to a second intermediate link, wherein the second intermediate link is positioned between the upper portion and the lower portion;
a third pulley rotatably coupling the second intermediate link to the lower portion to allow the second intermediate link and the lower portion to rotate independently of one another;
a first tension-bearing element having a first end and a second end, the first tension-bearing element substantially encircling each of the first pulley, the second pulley, and the third pulley in a first direction, wherein the second end of the first tension-bearing element is anchored to the lower portion; and
an actuator system coupled to the first end of the first tension-bearing element, wherein the actuator system is configured to apply a torque to the brace system.

18. The brace system of claim 17, wherein the actuator system includes a hydraulic actuator coupled to the first end of the first tension-bearing element.

19. The brace system of claim 17, further comprising a second tension-bearing element having a first end and a second end, the second tension-bearing element substantially encircling each of the first pulley, the second pulley, and the third pulley in a second direction.

* * * * *